United States Patent [19]
Steger et al.

[11] Patent Number: 5,101,670
[45] Date of Patent: Apr. 7, 1992

[54] AUTOMATED PROPORTIONAL INTEGRATED SAMPLING SYSTEM

[76] Inventors: Joette L. Steger, 105 Bishop Ct., Cary, N.C. 27513; Andy L. Blackard, 1410 Shawnee St., Durham, N.C. 27701; Raymond G. Merrill, 5116 Tudor Pl., Durham, N.C. 27713; Frank E. Butler, 1009 Sturidivant, Cary, N.C. 27511; Joseph E. Knoll, 4000 Buckingham Way, Apex, N.C. 27502; M. Rodney Midgett, 1018 Manchester Dr., Cary, N.C. 27511

[21] Appl. No.: 591,550

[22] Filed: Oct. 1, 1990

[51] Int. Cl.⁵ ............................................. G01N 1/00
[52] U.S. Cl. ................................................. 73/863.03
[58] Field of Search ......................... 73/863.01–863.03, 73/863.11, 863.31, 863.32, 863.81–863.86, 864.63, 864.91

[56] References Cited

U.S. PATENT DOCUMENTS

| | | | |
|---|---|---|---|
| 2,906,126 | 9/1959 | Brown | 73/863.02 |
| 3,719,081 | 3/1973 | Lynn et al. | 73/863.02 |
| 3,884,081 | 5/1975 | Griffith | 73/864.63 |
| 4,274,285 | 6/1981 | Purgold | 73/863.31 |
| 4,527,436 | 7/1985 | Jones | 73/863.84 |
| 4,580,453 | 4/1986 | Taylor | 73/863.84 |
| 4,615,468 | 10/1986 | Gay | 73/864.91 |
| 4,628,748 | 12/1986 | Jogan et al. | 73/863.01 |

FOREIGN PATENT DOCUMENTS

| | | | |
|---|---|---|---|
| 463027 | 3/1975 | U.S.S.R. | 73/863.32 |
| 1280464 | 12/1986 | U.S.S.R. | 73/863.01 |

*Primary Examiner*—Robert Raevis
*Attorney, Agent, or Firm*—Klauber & Jackson

[57] ABSTRACT

A sampling system for integrated proportional sampling of a fluid stream. The system includes a syringe-like sample container having an inlet/outlet at one end and a piston therein displaceable to fill and discharge the container. The inlet of the sample container is connectable to the fluid stream, for withdrawing samples to the container. Flow sensor means positionable in the fluid stream are provided, for continuously measuring the flow rate of the stream and providing a continuous first control signal varying in accordance with the measured flow rate. Piston drive means withdraw the syringe piston at a rate in accordance with the first control signal, and limit means stop the withdrawing piston at a predetermined end point in its axial movement. The sample container is coupleable and uncoupleable as a unit from the system, to enable the container to be transferred and interconnected for discharge to a sample analyzer while maintaining the collected sample intact between its inlet/outlet and piston, and thereby out of contact with ambient air.

8 Claims, 6 Drawing Sheets

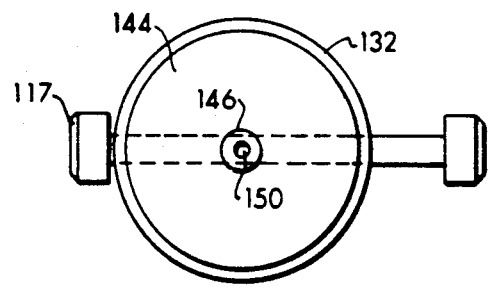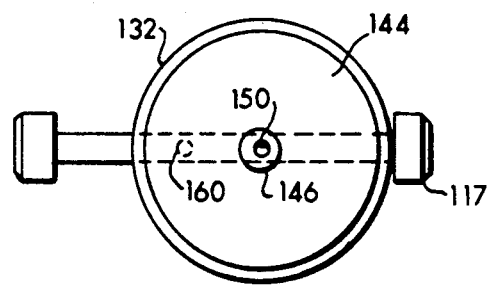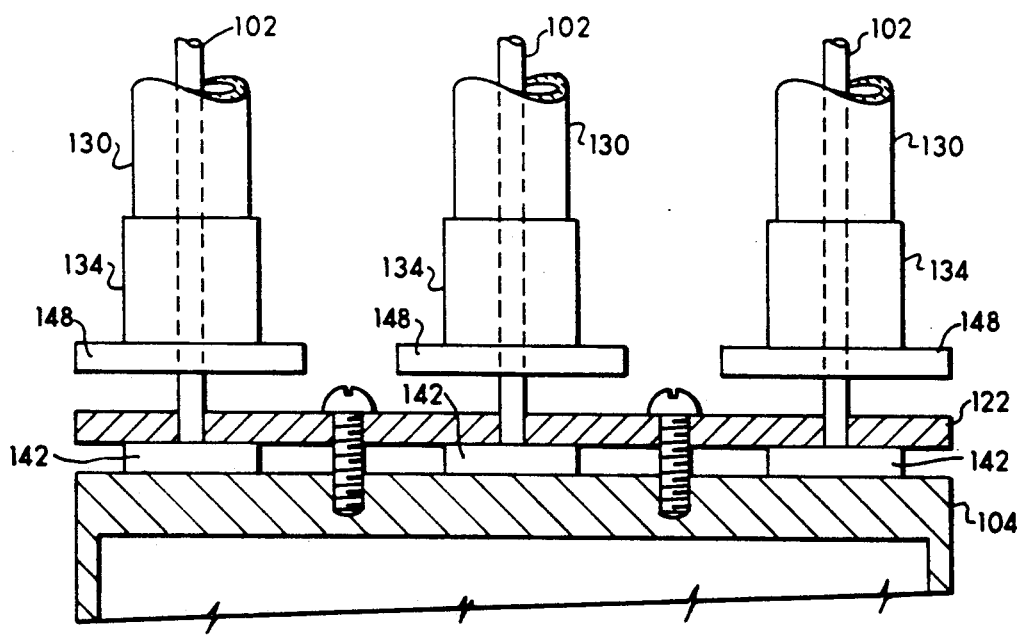

AUTOMATED PROPORTIONAL INTEGRATED SAMPLING SYSTEM

BACKGROUND OF INVENTION

This invention relates generally to chemical analysis and sampling, and more specifically relates to sampling and analytical procedures for use with source and process streams.

Because of an ever increasing awareness of the environmental dangers posed by discharge of toxic chemical compounds and compositions into bodies of water such as rivers, streams, ponds and the like, an increasing need has arisen for sophisticated apparatus for use in monitoring the undesired species of contaminants which may be present in an aqueous environment of interest. In many instances, the contaminants monitoring sought to be achieved is a consequence of voluntary efforts by industry or citizen groups. More frequently, however, it is found that municipal, state and/or federal agencies are involved in such procedures or promulgate standards which require the monitoring activity. For example, the Environmental Protection Agency (EPA) has been involved in the promulgation of emissions standards, the objective of which is to control various emission sources of volatile organic compounds (VOC's) listed therein as hazardous wastes. Under the Resource Conservation and Recovery Act (RCRA), non-point sources such as ponds, land treatment areas, and waste water treatment systems, are the focus of considerable research activities designed to access VOC emission characteristics.

The problem of adequately and accurately sampling process steams is a particularly acute one. Current grab sampling techniques for volatile and semi-volatile organic emissions sampling, commonly do not adequately address integration of the cyclic variation of flow or concentrations in liquid process systems. Grab sampling data pertaining to volatile organics must also be manually corrected for changes in flow rate of the stream under survey. Manual correction of data is labor intensive and subject to calculation error. The grab sampling and analysis methods are also labor intensive for cyclic process sampling, due to the large number of samples that must be taken and analyzed to account for flow and concentration variation in process streams over time.

For the foregoing reasons, automatic sampling apparatus of various types are increasingly being sought and used to sample liquid streams. Such devices can in principle be cost effective, versatile, and reliable, and can include capabilities for greater sampling frequency and the ability to integrate emissions over time. A number of different automated samplers are indeed commercially available, which vary in sophistication, performance, mechanical reliability and cost. However, to the present time, no single automatic sampling device has found to be ideally suited for most situations. Among other things, certain criteria are sought after in such a device. Among the variables which must be effectively compensated for or processed in such apparatus, are these:

1. the variation of water or waste water characteristics with time;
2. the variation of flow rate with time;
3. the specific gravity of liquid and concentrations of suspended solids;
4. the presence of large debris and floating materials in the source or process stream; and
5. the type of channel containing the stream, i.e. whether a duct, sluice or weir.

A further very significant problem arising in the prior art is generated by the mentioned need to measure volatile organics in the samples obtained from the stream or other aqueous source. In order to adequately and properly measure the VOC components, the sample containing same must be withdrawn and treated in such a manner as to avoid loss of the very volatile component the concentration of which is sought to be established. Prior apparatus has not adequately dealt with this very serious problem.

The prior art applicable to this invention is well shown in a number of United States patents. These include the following:

U.S. Pat. No. 3,985,028 to Yoshida, relates broadly to the concept of sampling a waste stream at a rate proportional to the flow of the stream being analyzed and providing an integration of the sample readouts. The apparatus described therein utilizes a flow meter to determine the rate of flow in the stream which is being sampled, and preferably converts the signal from the flow meter into a pulse signal which operates a driving circuit for a pulse motor. The pulse motor in turn operates at a rate determined by the output of the flow meter, a cylinder and piston arrangement which draws the sample at a rate proportional to the flow in the stream. One or more of such piston cylinder arrangements can be utilized. Yoshida also utilizes a predetermined fill period in operating each of its syringes; i.e. withdrawal of the sample is taken for a predetermined period. Yoshida also storing container is separate from the container in which the samples are initially collected.

In U.S. Pat. No. 4,091,675 to Jennison, the head of a liquid is sensed by capacitor probes, and a voltage is generated for driving a stepping motor, which in turn is used to operate a pump controlling the sampling.

Lapidot, U.S. Pat. No. 3,940,933 discloses apparatus for obtaining from a fluid stream a sample having a volume that is proportional to the flow rate of the fluid stream.

U.S. Pat. No. 4,791,820 to Lawrence et al, discloses an apparatus module for volatile collection.

U.S. Pat. No. 3,719,081 to Lynn et al discloses an apparatus where an effluent is discharged into a flume to float past a selectively operable sampling device, and an adjacent probe develops and transmits to a remote control point a signal, the amplitude of which is proportional to the effluent flow rate. At the control point the signal is applied to an integrator which produces an output voltage proportional to the quantity of effluent which has passed the probe in the preceding interval. Each time the voltage reaches a predetermined value, a threshold circuit resets the integrator and pulses a first register to record the quantity of effluent for a given period and simultaneously pulses a presetable counter which produces a sampler enabling signal every time the counter reaches 0 and resets.

Other patents of interest pertinent to this technology include: U.S. Pat. Nos. 4,766,550 to Byers et al: 3,930,414 to Russell: 3,253,469 to Normal: 3,546,945 to Collins; 3,929,017 to Kowalski: 3,813,945 to Krumal: 4,207,450 to Mittleman; 2,963,114 to Zucker et al: and 2,927,465 to Smith et al.

In accordance with the foregoing, it may be regarded as an object of the present invention to provide an automatic proportional integrated sampling system for collection of representative samples from liquid streams for subsequent volatile and semi-volatile compound analysis, which device enables substantially continuous integrated sampling.

A further object of the present invention, is to provide an automated proportional integrated sampler of the foregoing character, which includes features enabling maintenance of a gas tight sample reservoir with substantially zero headspace, and protection of the sampling reservoir against light and high temperature during field sampling.

A still further object of the present invention, is to provide apparatus of the foregoing character which includes features enabling same to sample at a rate which takes account of variation of flow rate with time.

A yet further object of the invention, is to provide an automated proportional integrated sampling system which may readily operate under full computer control and which includes the ability to be preset for sampling at specified times, as for example during unattended periods, night time and the like.

It is yet another object of the invention, to provide a system of the foregoing character which provides means for selecting the length of the sample period and for integrating sample collection over that period.

A still further object of the invention, is to provide apparatus of the foregoing character in which both liquids and gases can be collected in filtered or unfiltered appropriate sample containers, such as gas tight syringes, canisters, bags or bottles.

A yet further object of the invention, is to provide sampling apparatus of the aforementioned character including temperature control features, which in conjunction with the sample containers enable the apparatus to maintain the integrity of the samples, wherein the apparatus may measure and record the various sampling parameters such as flow temperature and pH, and wherein several sampling functions can be performed simultaneously.

A still further object of the invention, is to provide apparatus of the foregoing character which by virtue of its automated features and dependability of operation, act to substantially reduce an end user's sampling-/analytical costs, and which will still maintain accuracy close to that achieved by use of the standard grab sample methodology.

SUMMARY OF THE INVENTION

Now, in accordance with the present invention, the foregoing objects, and others as will become apparent in the course of the ensuing specification, are achieved in a sampling system which enables integrated proportional sampling of a fluid stream. Pursuant to the invention, one or more syringe-like sample containers are provided having an inlet/outlet at one end and a piston therein displaceable to fill and discharge the container. Means are provided for connecting the inlet of the sample container to the fluid stream to enable withdrawing of samples to the container. Flow sensor means are disposed in the fluid stream for continuously measuring the flow rate of the stream and providing a continuous first control signal which varies in accordance with the measured flow rate. The syringe piston is driven by piston drive means which act to withdraw the piston at a rate in accordance with the first control signal; and limit means are provided for stopping the withdrawing displacement of the piston at a predetermined end point in its axial movement. The sample container is coupleable and uncoupleable as a unit from the inlet-stream connecting means and piston drive means, to enable the sample container to be transferred as a unit and interconnected for discharge to a sample analyzer, while yet maintaining the collected sample intact between the inlet/outlet and the piston, and thereby out of contact with ambient air.

In a further aspect of the invention, means may be provided for maintaining the temperature of the collected samples at a predetermined value.

The system may further, incorporate timer means for initiating sampling at a preset time and for a preset period.

The system may be completely operated under computer control, and includes means for operator setting of an initial nominal sampling rate.

In accordance with a further aspect of the invention, means responsive to the said first control signal will terminate sampling when the signal falls below a predetermined threshold value.

The piston drive means preferably comprises a stepping motor, connected to displace the piston in accordance with the output of the motor; and means for providing drive pulses to the stepping motor at a rate proportional to the first control signal.

BRIEF DESCRIPTION OF DRAWINGS

A fuller understanding of the present invention may now best be gained by a reading of the ensuing specification, and by simultaneous review of the drawings appended hereto in which:

FIGS. 7 and 8 are transverse cross-sectional views through the valve of the syringe sample container, respectively showing the valve in its open and closed conditions;

FIG. 9 is an enclosed, partially sectional view, showing the manner in which the plungers of a plurality of sample containers are commonly driven by the syringe carriage drive of the apparatus of FIG. 2;

DESCRIPTION OF PREFERRED EMBODIMENT

Figure 1:
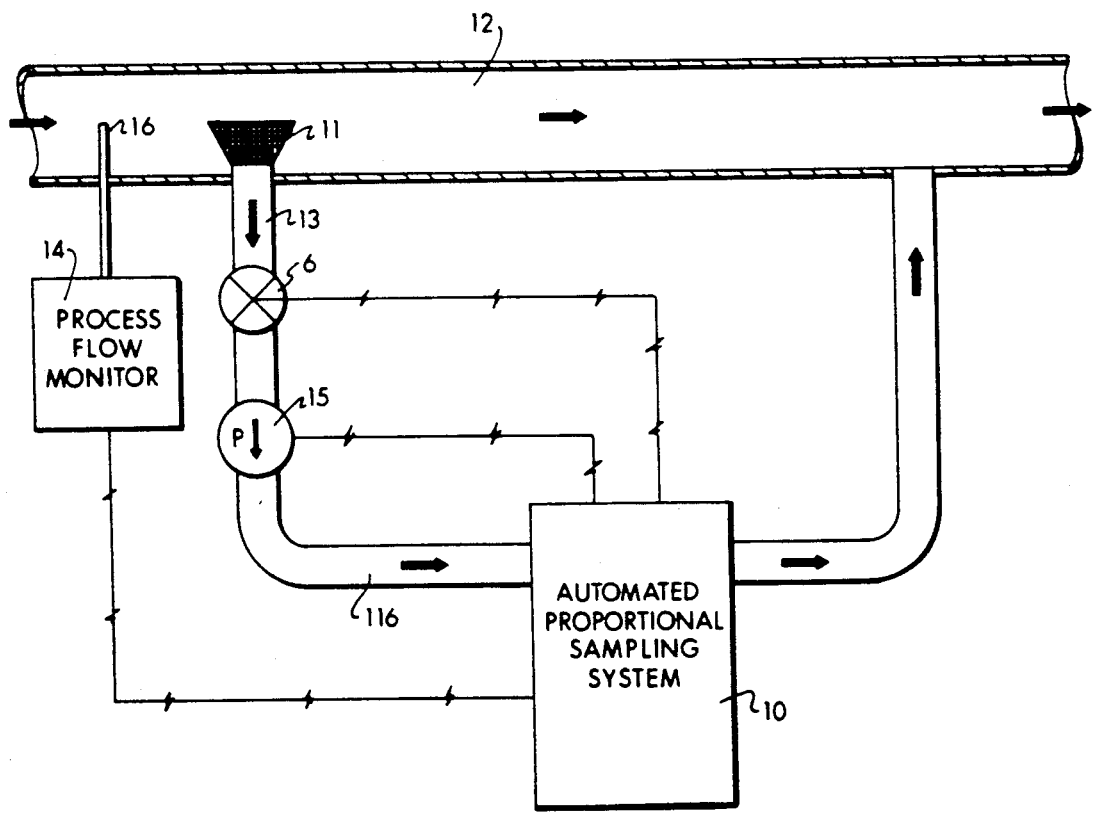
FIG. 1 is a schematic block diagram illustrating a typical installation in which the system of the present invention finds application.

In FIG. 1 a simplified block diagram appears showing the manner in which an automated proportional sampling system 10, in accordance with the present invention, is utilized in a typical installation. System 10 is illustratively shown being utilized to monitor the contaminant level in a fluid stream 12. Stream 12 can comprise an industrial discharge: or can comprise a natural stream, river, or the like; or can comprise a static aqueous body, a parameter of interest for which changes as a function of time, as for example the concentration level of a specified contaminant. A flowing industrial fluid stream, however, provides a representative environment in which the present system may be utilized, and for purposes of this discussion, the stream 12 may be considered to be of that nature.

The automated sampling system 10 performs its sample collection in direct proportion to a real-world process flow associated with a stream of this type. The system 10 uses a standard industrial electronic signal interface such that any type of flow rate such as mass flow rate, actual flow rate, or standardization flow rate, or flow velocity may be used as the basis for the proportional sampling. In the present instance, a process flow monitor generally shown at 14 is provided with a probe 16 extending into the fluid stream 12. Probe 16 which may be of standard construction known in the art (e.g. in the patents cited infra), thus may measure the flow of fluid in stream 12. An electrical output signal indicative of the instantaneous rate of flow is provided to system 10 from probe 16 by means which will be hereinafter described. Prior to sample collection, a flow monitor calibration is performed and then the average flow of the system is measured over a user specified period of time. The nominal sampling rate is determined by this average flow and the user specified period of time for sampling to occur. Optionally, the system 10 includes means for stopping sample collection when the process flow falls below preset lower limit of flow for which the stream may not represent normal operating conditions.

A series of sample containers are provided in system 10, which will be more fully described in connection with FIGS. 3 through 6. Positional sensing is used to determine when the sample containers used with the invention have completely filled, and the sampling should be stopped and the containers sealed. The nominal sampling time supplied by the user is not used by system 10 for determining when to stop sampling. This desired sampling time is used instead to determine a nominal sampling rate, the rate at which to extract a sample from the stream when the flow of the stream is exactly equal to the measured average process flow. Additionally, the system 10 includes means for monitoring the temperature of the sample compartment forming part of same, in order to control the sample compartment cooling system. The automated system indicates when the sample syringe is cooled sufficiently for sample collection. Samples are provided to the system 10 by being withdrawn through screen 11 into duct 13. A pump 15 and sample shutoff valve 6 are provided, each connected to and being under the control logic of system 10, to allow flow from the stream 12 to pass to the system 10 during the sampling operation.

Figure 2:
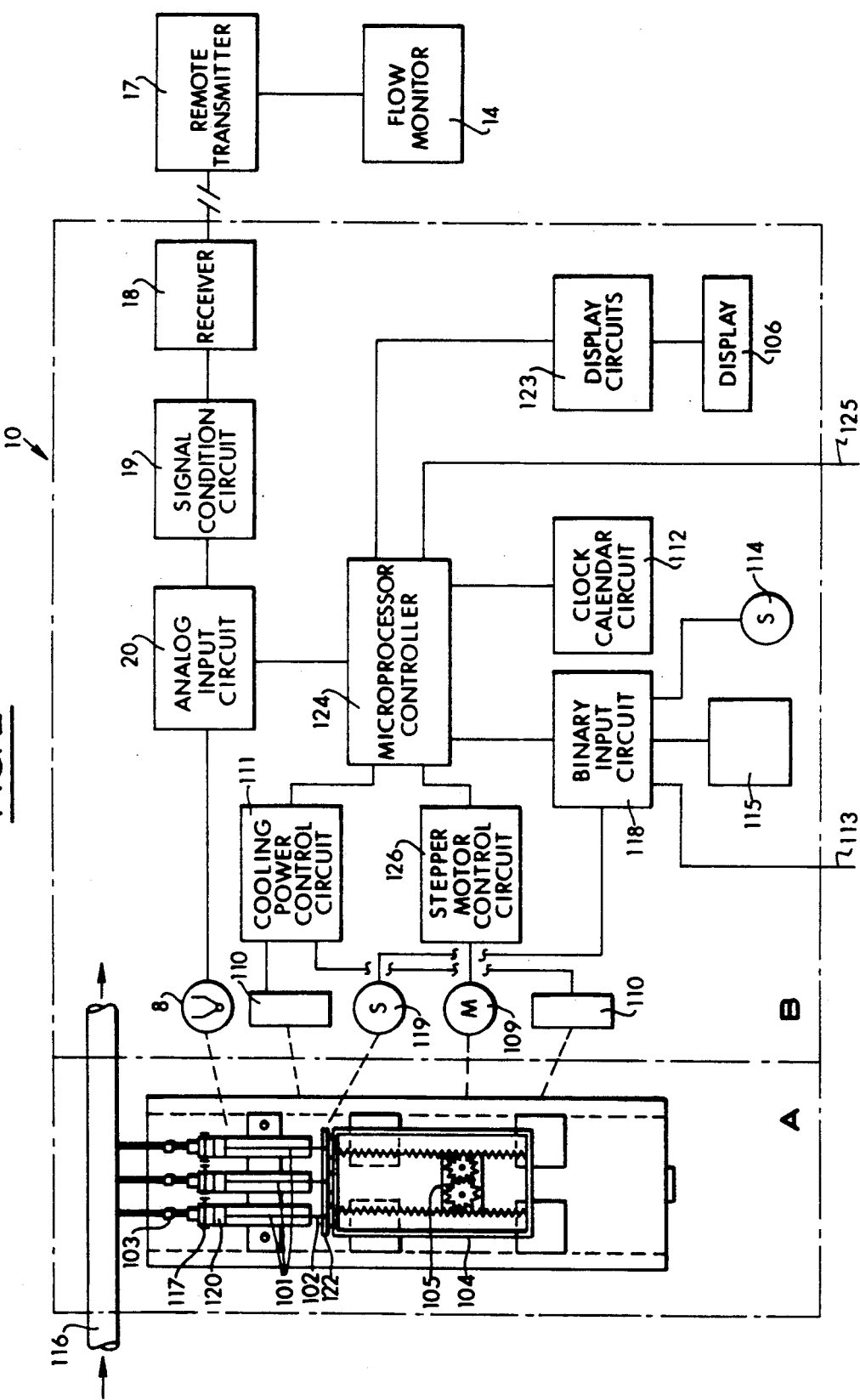
FIG. 2 is a schematic block diagram, partially mechanical and partially electrical in nature, setting forth the basic elements of an automated proportional sampling system in accordance with the present invention.

Referring to the simplified schematic block diagram of FIG. 2, the automated proportional sampling system 10 typically uses one or more special air-tight syringe-type sampling vessels referred to herein as the "sample syringes", which extract an aliquot of samples from a flow-through slipstream manifold 116 (See FIG. 1). Each syringe 101 is connected to the manifold 116 by a threaded fitting 103. Pistons 120 present in each syringe are driven by plunger rods 102 which are commonly attached at bracket 122 to a motor-driven carriage 104 which retracts the syringe plunger rods in order to extract samples from the manifold. This carriage 104 is driven by a stepping motor 109 via a reducing gear arrangement including rack and pinion drive 105, to provide the small plunger retraction rate required to fill the syringe over an extended period of time.

Sampling system 10 is constructed in a multi-compartment housing. A refrigerated compartment schematically indicated at A, contains the sample syringes 101 and the syringe drive mechanisms already discussed. An electronics compartment schematically indicated at B, contains the microprocessor controller 124 and power supplies (not shown). The microprocessor controller 124 serves a central function in the operation of the present apparatus. It provides for interfacing operator interactions, determining process flow rate, and controlling the rate of the stepping motor 109 and the refrigeration system operation for compartment A. Microprocessor controller 124 is provided with an accurate time base, i.e. from a clock calendar circuit 112 for determining real time and calendar date for unattended start-up and for recording the date and time. The microprocessor controller 124 performs all run-time calculations for flow monitor signal calibration, sampling rate determination, and determination of motor control parameters.

Microprocessor controller 124 activates and controls the hardware and software systems which carry out specialized tasks. Each of these specialized tasks is handled by a specific sub-component of the control software. Compartment A is cooled by thermoelectric cooling elements schematically shown at 110. These are interconnected in a third compartment (not shown) which contains conventional heat dissipators and a circulation fan which allows the thermoelectric cooling elements to pump heat from compartment A. Controller 124 maintains a preset temperature in compartment A via conventional thermostat 8 mounted therein, through a cooling power control circuit 111. Sample collection in system 10 is effected in direct proportion to an industrial process fluid flow as measured by process flow monitor 14 and the probe 16 which is installed in the stream of interest, i.e., representatively stream 12 of FIG. 1. The system 10 uses a standard industrial electronic signal interface such that any type of flow rate, mass flow rate, actual flow rate or standardized flow rate or flow velocity may be used as the basis for proportional sampling.

The operation mode switch 114 provides the principal means for the system operator to control automated sampler system 10. Mode switch 114 has four settings: STANDBY, SETUP, AVERAGE FLOW, and COLLECT. The position of switch 114 determines the set of actions which the automated sampling system may carry out. These individual actions are displayed in menu form on the sampler output display panel 106 which is controlled by controller 124 via display circuits 123. The system operator selects among these various control options and enters any required numerical factors by use of an alphanumeric keypad 115 with the input being rendered digital at binary input circuit 118.

Prior to sample collection, a flow monitor calibration procedure is carried out to allow the system 10 to determine an accurate measure of process flow. This is performed with the operation mode switch 114 in the SET-UP position.

Manual control of the stepping motor drive is also provided in the SET-UP mode to assist with installation of the sample syringes 101. System 10 optionally also includes the ability to terminate sample collection when the process flow falls below a preset lower limit of flow for which the stream may not represent normal operating conditions. This option may also be selected in the SET-UP mode. Also, while in the SET-UP mode, the operator supplies an approximate period of time over which the automated sampler will fill the sample syringes 101. This is the so-called "nominal" period of setting.

Before sampling can begin, an average process flow for the process is determined by allowing the system to measure the process flow over a user-controlled period of time. This is performed by placing the operating mode switch 114 in the AVERAGE FLOW position. Thereupon the nominal sampling rate is determined by the microprocessor by using this average measured flow and the operator specified approximate sampling time duration. A position sensor 119 which can be a microswitch or a capacitatively coupled switch or sensor responsive to the longitudinal position of carriage 104 is used to determine when the sample syringes 101 have completely filled and sampling should be stopped and the syringes are to be sealed. However, the approximate sampling time supplied by the operator is not used directly by system 10 for determining when to stop sampling. This desired sampling is used instead to determine a nominal sampling rate. The nominal sampling rate is the rate at which to extract a sample from the stream when the flow of the stream is exactly equal to the measured average process flow.

When the operator is ready to start sample collection, mode switch 114 is placed in the COLLECT position. The first determination system 10 makes is when to commence sample collection. The sampler is programmable in the sense that it may be made to start sample collection at a pre-set time unattended. Most frequently, this is used to start sample collection on a certain day and time unattended, although it may also be used to carry out samplings at intermittent periods as for example preselected hours during the nighttime or i.e. over a continuous nighttime period or during spaced periods during the night. Optionally, the operator can trigger the start of sample collection manually from keypad 115.

Alternatively, the present system 10 may be programmed to start sample collection when the process flow exceeds some threshold value or upon receipt of an external signal to start sample collection. A yet further option allows the start of sample collection to be triggered by an externally generated signal introduced by the external sample start signal provided at connection 113. The start of sample collection is recorded on the sampler's recording devices.

After sample collection has commenced, the automated sampler receives the measured process flow from flow monitor 14 (FIGS. 1 and 2) and compares the actual real-time flow to the average process flow which was determined prior to sampling. Flow monitor 14 may be connected to a remote transmitter 17, which is useful if the stream being monitored is distant from the remainder of the system. The resultant signal (which may be at a receiver 18) is detected at 19, and via analog input circuit 20 is provided to controller 124 (circuit 20 may also process the signal from thermostat 8). A sampling rate and the necessary motor control parameters are calculated and provided to the software subsystem which controls syringe drive motor 109. If a lower limit for process flow is specified by the operator, sample collection will be suspended whenever the process flow falls below that limit. This event is registered on the sampler's recording devices. While the sampler is in COLLECT mode, an output data stream is provided to output port 125 for transmission to an external computer system, recording device, or telemetry.

When the syringe drive carriage 104 has moved to a preset longitudinal position indicating that the syringes are filled, position sensor 119 is actuated; the microprocessor controller 124 responding to the signal that the sample syringe has filled, provides a stop signal to the stepper motor control circuit 126 to stop the syringe drive motor 109, and sampling will stop. This event is recorded on the output devices.

Figure 10:
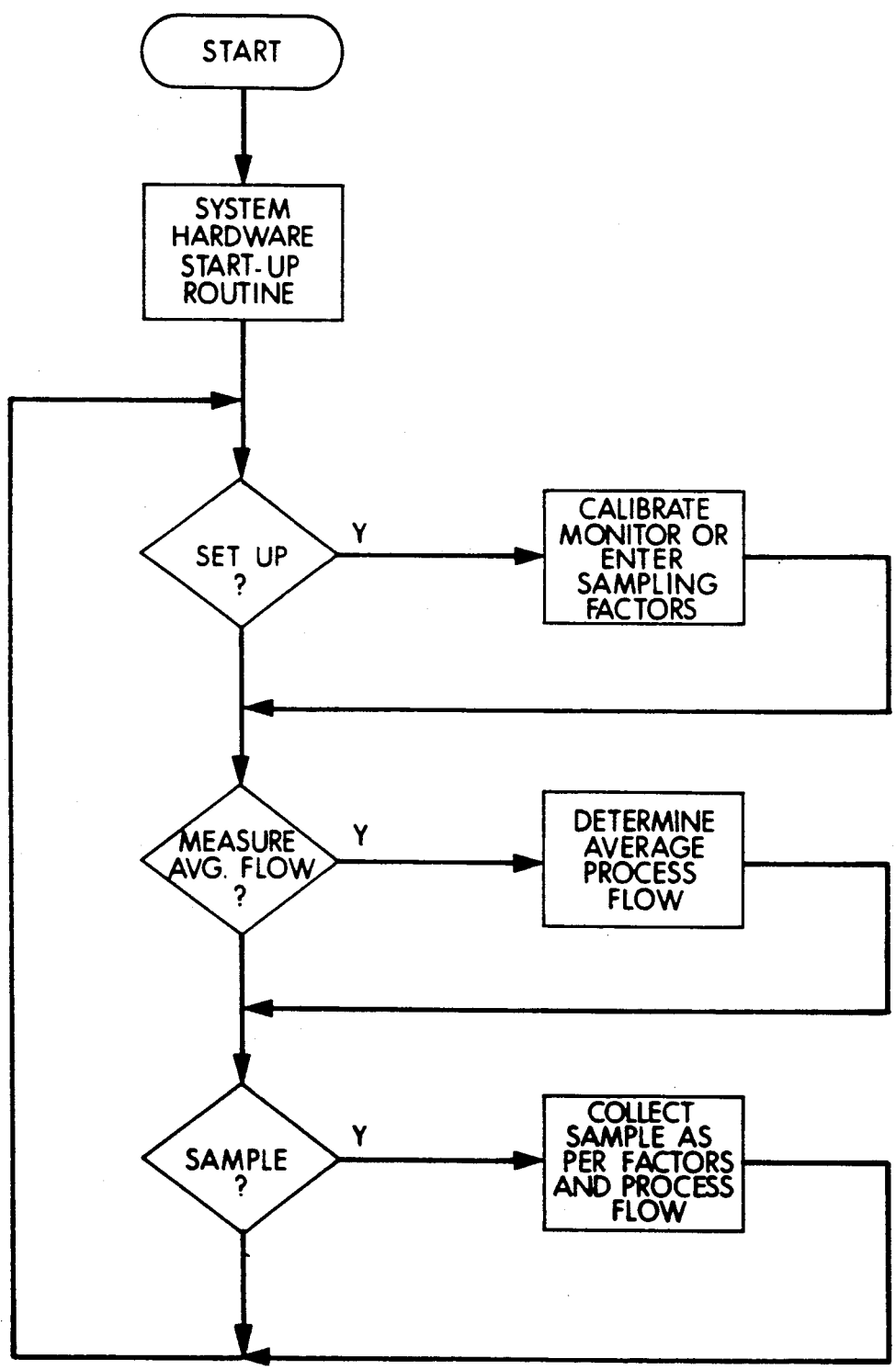
FIG. 10 is a schematical flow diagram depicting the main control algorithm which may be utilized in the present invention.

FIG. 10 presents a schematic flow diagram for the main control algorithm for system 10. This and other software for sampler operation, measurement, and control are permanently stored in firmware form within the microprocessor controller 124. This main control algorithm performs a one-time hardware start-up routine when power is first applied to the system 10. This start-up routine retrieves previously stored sampling and operation factors from battery-powered "nonvolatile" memory and also acts to initialize control of the sampler hardware. Next the main control algorithm proceeds into an endless control loop wherein the state of the mode switch 114 is perpetually checked. If the mode switch 114 is moved from the STANDBY position to one of the other three settings (SET-UP, AVERAGE FLOW, or COLLECT) software control passes to a specific routine for each of these three modes.

In the SET-UP mode, the user may use the key pad 115 to manually operate the sampler in order to install the sampling syringe(s) 101 or to specify the desired sampling duration and other sampling factors.

In the AVERAGE FLOW mode, the system will measure the signal from the process flow monitor 14 and determine an average flow rate for the fluid stream. This average flow is used to calculate a nominal sampling rate for the desired sampling duration.

Figure 11:
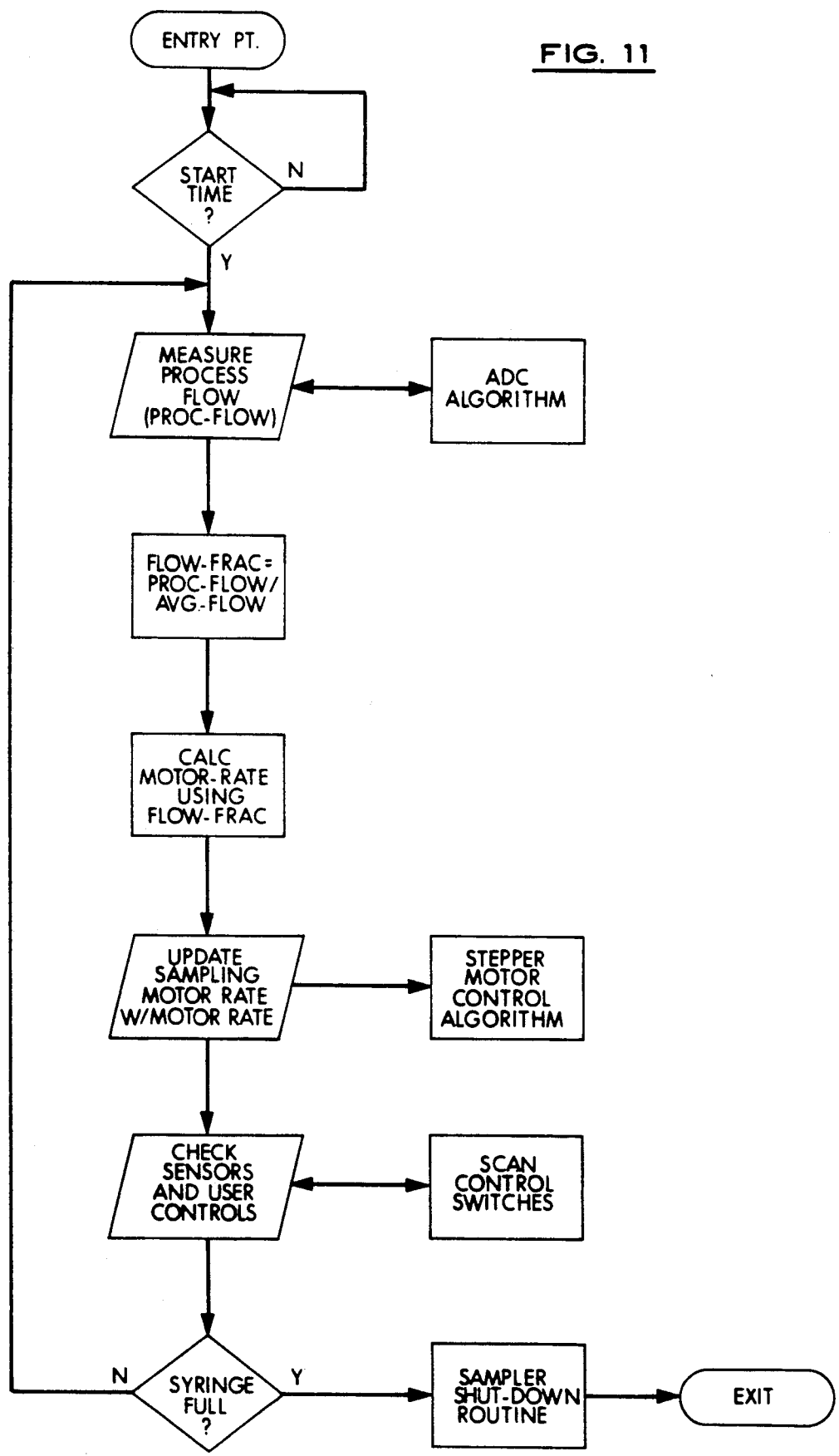
FIG. 11 is a flow diagram similar to FIG. 9, but showing a sample mode algorithm for use in the invention.

In the SAMPLE mode, the system checks the specified start time versus the clock 112 and delays, if appropriate, until the desired start time and then begins proportional sample collection. The detail of the SAMPLE mode algorithm is shown in FIG. 11. After sample collection has commenced, an analog-to-digital conversion (ADC) circuit 20 provides a digital measurement of the process flow monitor 14 signal. This signal is compared to the previously determined, average flow rate, and the desired sampling rate is calculated for the instantaneous process flow. Next a set of sampling motor parameters are determined which would cause the sampling motor 109 to move at a rate which would extract sample at the desired rate. These sampling motor parameters are passed to a special stepper motor control algorithm which interfaces directly with the stepper motor control circuit 126 to perform the actual motor control. Next the SAMPLE algorithm checks the sampler's position sensor 116 to determine if the syringe(s) are full and sample collection should stop. If the syringe(s) are full, the sampler will park the syringe motor to maintain the sample, record the time, and display a prompt on the display 106 that sample collection has completed. The SAMPLE mode algorithm will now stop and pass control back to the main control algorithm shown in FIG. 10.

When sample collection is completed, stepping motor 109 is thus placed in a "park" position to preclude any movement of the syringe plungers 102 from changes in the process stream pressure. The completion of sampling is indicated on the display panel 106.

Figure 3:
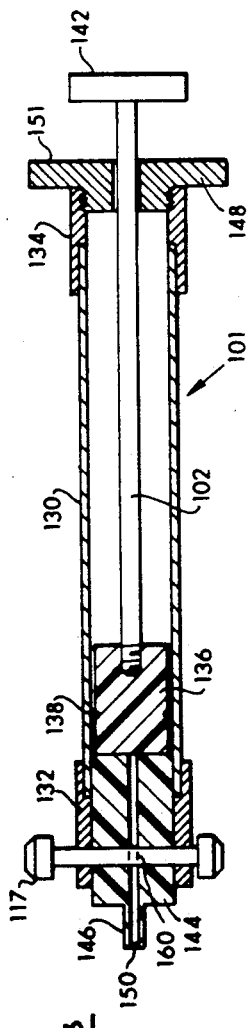
FIG. 3 is a schematic, partially sectioned view showing a syringe sampling container which may be utilized with the present invention.

Referring to both FIGS. 2 and 3, the operator prepares a sample syringe 101 for transportation to a spaced analytical device, by first closing the upstream valve 6 on the process line (FIG. 1) leading to the sampling manifold 116. Next the integral syringe shutoff valves 117 are closed and the syringes are disconnected from the manifold at the threaded fittings 103. The syringe plunger rods 102 are now disconnected from drive carriage 104 and are unscrewed from the syringes, leaving the plunger seal (piston 136) in position. The removed syringes 101 are then placed in a refrigerated container for transportation to the analytical instrumentation, the latter being present, for example, at a standard analytical laboratory. In this connection it is to be appreciated that the present system 10 may typically be installed at a field location while the analytical laboratory itself may be at a completely separate location, which in some instances can be located many miles from the sampling point.

A key aspect of the present system indeed involves the syringe sample containers 101 proper. These components serve not only as a means for collecting and holding samples withdrawn from the process stream; but of equal importance, serve as the de' facto sample container for the collected samples which are to be transported to the analytical laboratory for examination. As will be further evident in the ensuing, these containers assure that the collected samples maintain their integrity from the time they are collected, to the time they are withdrawn for analysis. In particular, unlike prior devices, it will become evident that no head space is ever created in these containers—as would encourage the loss of the volatiles which are intended to be subject to analysis.

Referring especially to FIGS. 3 through 6, schematic longitudinal cross-sectional views appear of the syringe sample container 101 utilized in accordance with the present invention. Syringe sample container 101 is but one of a series of such containers which are mounted in parallel in the system. As seen in FIG. 3, the container 101 consists of a transparent barrel 130, preferably of glass or of chemically resistant plastic, having metal bands 132 and 134 at each end. A piston 136, preferably of a chemically inert material such as TEFLON synthetic resin polymers, is mounted for longitudinal movement in barrel 130. Sealing rings, in the form of a pair of O-rings 138 are mounted about the periphery of piston 136 to form a liquid and airtight seal with the internal walls of barrel 130. This seal should be effective over the entire temperature range from at least 0° to 30° C., which are typical operating conditions for the sampling apparatus. A plunger rod 102 extends from piston 136 and is provided at its distal end with an enlarged knob-like portion 142 which engages with the syringe drive mechanism at bracket 122. The rod 102 is preferably threadingly received within the base of piston 136 so that it can be readily removed prior to transport o container 101.

The end 144 of the syringe sample container 10 which is to be connected to manifold 16 is provided with a simple frictional connection 146. This may also take the form of a conventional swage or pipe thread coupling. An enlarged plunger stop 148 is provided at the end 151 of container 101, which prevents the piston 136 from being blown or pulled out of the syringe barrel. This is threadingly received in the end of barrel 130 so that the plunger rod 102 may be removed from barrel 130 where required. An on/off shutoff valve 117 is also provided adjacent the inlet/outlet end 150 of the container. As seen in the cross-sectional views of FIGS. 7 and 8, displacement of the ON/OFF valve 117 by manual or automatic means acts to align or disalign the passageway 160 with the opening of inlet/outlet end 150 of container 101. Equivalent types of valves can be used for this purpose.

Figure 4:
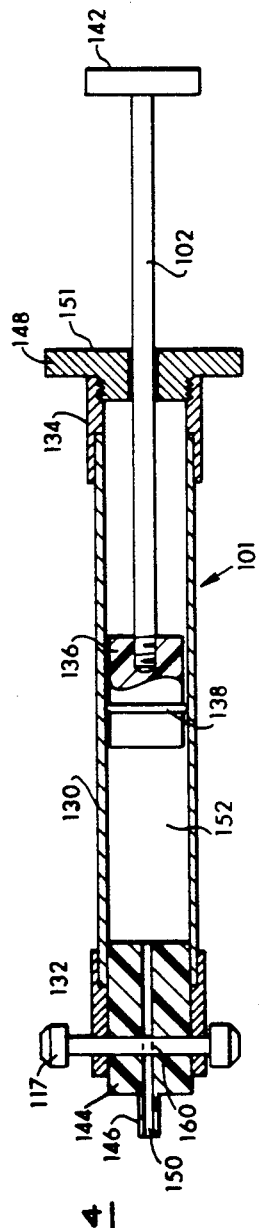
FIG. 4 is a schematic view similar to that of FIG. 3, showing the syringe sample container of FIG. 3 in an intermediate condition during sampling.
Figure 5:
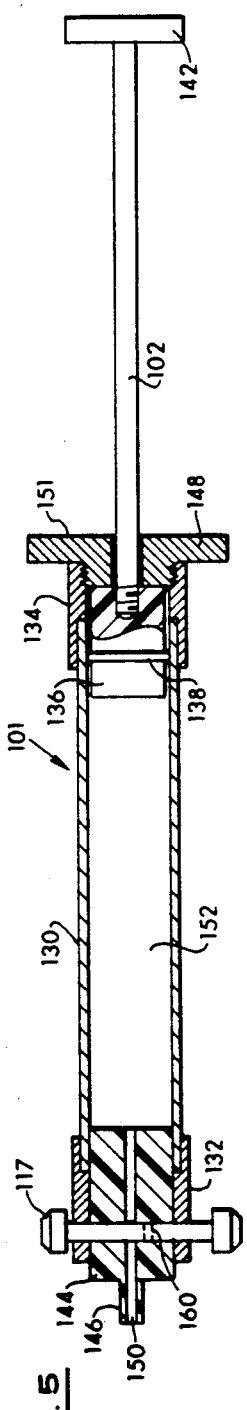
FIG. 5 is a further view similar to FIGS. 3 and 4, but showing the syringe sample container at completion of the sampling procedure.

In FIG. 3 the sample container 101 is shown in its configuration where it is mounted in the sample compartment prior to sampling. In FIG. 4 the configuration is shown during the course of sampling; i.e., the piston 136 has now been partially withdrawn to the right, drawing a sample into the space 152. At the completion of the sampling step, the syringe is fully withdrawn as shown in FIG. 5.

Figure 6:
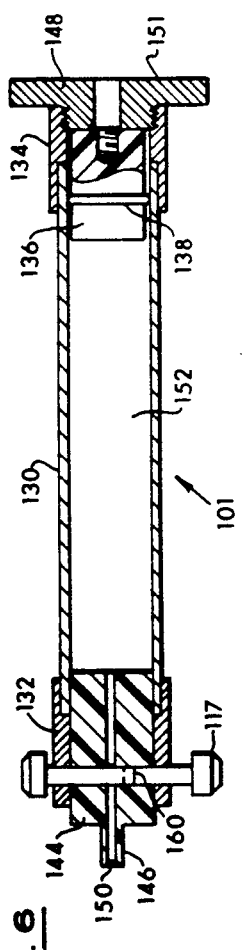
FIG. 6 is a further view of the syringe sample and sample container of FIGS. 3, 4 and 5, showing the syringe sample container prepared for shipping, transfer or transport.

In FIG. 6 the syringe sample container is shown as it is prepared for shipping and transport. The valve 117 is now in the OFF position (also in FIG. 5 upon completion of sampling) and the plunger rod 102 has been removed from piston 136 by unthreading of same. Piston 136 is seen to be at the extreme right-hand end of the sample container. With the valve 117 in the OFF position and the piston 136 at the extreme right-hand end, it will be evident that the sample is completely contained, ready for transport, and no air space exists. This is a unique aspect of the present invention, since there is no danger whatsoever that the volatile organics will in any way volatize and thereby change their concentration. At the same time, neither is there any requirement for moving the sample from its retention point to any other container—which would result in the creation of air space and loss of volatiles.

The syringe samples collected by the apparatus in the sample containers 101 are typically stored as they are at 4° C. until analysis. If the entire sample is not required for analysis the sample is mixed prior to analysis without exposing the sample to air. This is accomplished by attaching the sample container to a second gas-tight syringe through a zero dead volume connection. The sample is transferred between the syringes, and the turbulence created during the transfer causes the samples to be mixed. After mixing, the sample is returned to the collection syringe 101 and the collection syringe valve is closed and the mixing syringe disconnected. The sample is provided to a conventional analytical device via a luer lock connection and a purge flask. The sample is introduced into the purge flask through the luer lock connection. The valve for the lock is then turned 90° to allow the sample to pass through. When all of the sample is in the purge flask, the valve is turned back 90°. Then a helium purge is started.

While the present invention has been particularly described in terms of specific embodiments thereof, it will be understood, in view of the instant disclosure, that numerous variations upon the invention are now enabled to those skilled in the art which variations yet reside within the scope of the present teaching. Accordingly, the invention is to be broadly construed and limited only by the scope and spirit of the claims now appended hereto.

What is claimed is:

1. A sampling system for integrated proportional sampling of a fluid stream, comprising
   (a) at least one syringe-type sample container having an inlet and outlet at one end thereof and a piston therein displaceable to fill and discharge said container;
   (b) means for connecting the inlet of said sample container to said fluid stream, for withdrawing samples to said container;
   (c) flow sensor means positionable in said fluid stream for continuously measuring the flow rate of said fluid stream and providing a continuous first control signal varying in accordance with said measured flow rate;
   (d) piston drive means for withdrawing said syringe piston at a rate in accordance with said first control signal; and
   (e) limit means for stopping the withdrawing displacement of said piston at a predetermined end point in its axial movement;
   (f) said sample container being coupleable and uncoupleable as a unit from said stream connecting means and said piston drive means, for permitting said sample container to be transferred and interconnected for discharge to a sample analyzer while maintaining the collected sample intact between said inlet and outlet and said piston, and thereby out of contact with ambient air.

2. A system in accordance with claim 1, further including means for maintaining the temperature of said collected sample at a predetermined value.

3. A system in accordance with claim 1, including timer means for initiating sampling.

4. A system in accordance with claim 1, further including means for operator setting an initial nominal period of sampling time.

5. A system in accordance with claim 4, further including means responsive to said first control signal, for stopping sampling when said signal falls below a predetermined threshold value.

6. A system in accordance with claim 1, wherein said piston drive means includes a stepping motor connected to displace said piston in accordance with the output of said motor; and means for providing drive pulses to said motor at a rate proportional to said first control signal.

7. A system in accordance with claim 6, wherein said drive means includes a carriage connected to said piston and driven by said stepping motor.

8. A system in accordance with claim 7, wherein said sample container is one of a plurality of sample containers, each being driven in parallel by said stepping motor and said carriage.

* * * * *